United States Patent [19]

Jorn et al.

[11] Patent Number: 4,481,305

[45] Date of Patent: Nov. 6, 1984

[54] PROCESS FOR THE PREPARATION OF HYDROCARBONS

[75] Inventors: Ernest Jorn, Lyngby; Jens R. Rostrup-Nielsen, Virum, both of Denmark

[73] Assignee: Haldor Topsoe A/S, Lyngby, Denmark

[21] Appl. No.: 529,796

[22] Filed: Sep. 6, 1983

[30] Foreign Application Priority Data

Sep. 7, 1982 [DK] Denmark ............................ 3990/82

[51] Int. Cl.$^3$ ........................... C07C 1/04; C07C 1/20
[52] U.S. Cl. .................................... 518/705; 518/711; 518/707; 518/713; 518/714
[58] Field of Search ............... 518/705, 707, 711, 713, 518/714

[56] References Cited

U.S. PATENT DOCUMENTS 4,011,275  3/1977  Zahner .............................. 518/713
4,138,442  2/1979  Chang et al. ....................... 518/713

Primary Examiner—Howard I. Mars

Attorney, Agent, or Firm—Lawrence Rosen

[57] ABSTRACT

Hydrocarbons and especially as gasoline are prepared by the catalytic conversion in two subsequent reactors of a synthesis gas containing hydrogen and carbon oxides and having a mole ratio $CO/H_2$ above 1 and when the conversion commences a mole ratio $CO/CO_2$ of 5 to 20. In the first reactor, which is preferably a cooled reactor, the synthesis gas is converted into a methane-containing first intermediate and this at least partly further into a second intermediate containing dimethyl ether, at 5–100 bar and 150°–400° C., in the presence of catalyst(s), the effluent from this reactor is combined with a recycle stream containing low boiling components of the effluent from the second reactor, and then passed to the second reactor, which is adiabatic, where the conversion of the second intermediate is carried out at substantially the same pressure as in the first reactor and 150°–600° C. in the presence of a catalyst, preferably a zeolite catalyst, converting said intermediate partly into hydrocarbons, preferably hydrocarbons that are liquid at NTP conditions.

10 Claims, 1 Drawing Figure

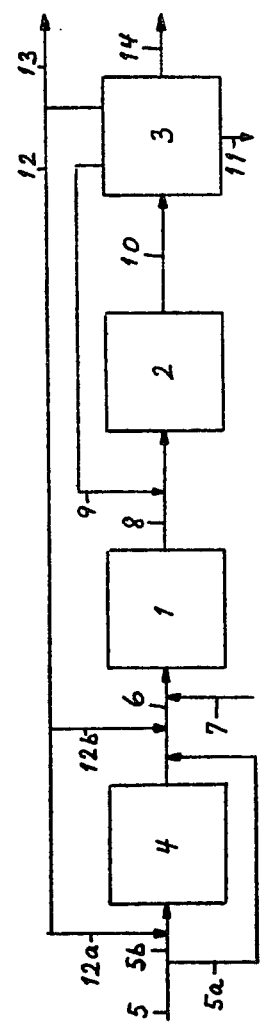

PROCESS FOR THE PREPARATION OF HYDROCARBONS

FIELD OF THE INVENTION

The present invention relates to the preparation of hydrocarbons by catalytic conversion in more than one step of a synthesis gas containing hydrogen and carbon oxides.

The invention especially relates to the preparation of hydrocarbons being liquids at normal temperature and pressure (NTP), particularly of synthetic high octane gasoline.

BACKGROUND OF THE INVENTION

The increasing demand for gasoline and other light petroleum fractions and the increasing lack of crude oil in recent years have caused an increased interest in preparing the desired products from alternative raw materials. There has already been described, i.a. in the patent literature, a large number of processes for preparing various petroleum fractions from various fossil fuels.

According to one of these processes hydrocarbon mixtures, including high octane gasoline, are prepared directly from lower alcohols and/or corresponding ethers by the catalytic reaction over synthetic zeolite catalysts. The process and the catalysts are described, i.a., in the U.S. Pat. Nos. 3,702,886, 3,709,979, 3,832,449, 3,899,544 and 3,011,941. The alcohols and/or ethers usable as starting materials may have been prepared in separate plants. It has been found advantageous, however, to integrate the process for the preparation of hydrocarbons by the aid of zeolite catalysts with a process for preparing the said alcohols and/or ethers from a suitable raw material such as natural gas or coal. Such integrated processes have already been described and especially two of them have been the subject of interest. In one of them a synthesis gas containing hydrogen and carbon oxides is converted via methanol (MeOH) into hydrocarbons, and in the other the conversion into hydrocarbons takes place via methanol/dimethyl ether (MeOH/DME). The conversion of MeOH is essentially according to the reaction $$CH_3OH \rightarrow (CH_2) + H_2O \qquad (5)$$

and that of DME according to $$CH_3OCH_3 \rightarrow (CH_2)_2 + H_2O \qquad (6)$$

In cases where it is desired to accomplish the integrated hydrocarbon synthesis at a comparatively low pressure, e.g. at a pressure of the order of magnitude of 30 bar, which occurs in industrial coal gasification plants, the degree of conversion in a process via MeOH will be comparatively low because of equilibrium conditions in the reaction:

$$CO + 2H_2 \rightleftharpoons CH_3OH \qquad (1)$$

It will therefore be advantageous to carry out the reaction via MeOH/DME:

$$CO + 2H_2 \rightleftharpoons CH_3OH \qquad (1)$$

$$2CH_3OH \rightleftharpoons CH_3OCH_3 + H_2O \qquad (2)$$

whereby the degree of conversion is increased because of more favourable equilibrium conditions. At the same time the process exhibits only slight pressure dependency.

Such a process for conversion via MeOH/DME is described in U.S. Pat. No. 3,894,102. In the process according to that specification a mixture of carbon monoxide and hydrogen is brought into contact with a catalyst mixture consisting of a methanol synthesis catalyst and an acidic dehydration catalyst in a first step to form an intermediate having a high content of DME. The intermediate or part thereof is thereafter reacted in a second step over a zeolite catalyst to form a product containing high octane gasoline. The process according to the patent specification may be accomplished according to a number of alternative embodiments which, e.g., may be subdivided as follows:

(A) The entire amount of intermediate from the first step is conducted to conversion in the second step and recycling is not employed.

(B) One or more components of the intermediate from the first step is conducted to conversion in the second step and the remaining components are removed and/or recycled to the inlet to the first step.

Both embodiments (A) and embodiments of type (B) entail drawbacks.

The embodiment (A) gives a low degree of conversion of the synthesis gas because recycling is not employed.

Embodiments of the type (B) are uneconomic in operation and require large investments because the fractionation of the intermediate from the first step is complicated and requires cooling to a low temperature of the entire amount of intermediate and renewed heating of the part of the intermediate to be reacted further in the second step.

It has now been found that in the process according to the present invention one is not only able to avoid the drawbacks described but also able to achieve further advantages.

BRIEF DESCRIPTION OF THE INVENTION

The invention relates to a process for the preparation of hydrocarbons by the catalytic conversion in more than one step of a synthesis gas containing hydrogen and carbon oxides and having a $CO/H_2$ mole ratio above 1 and, after having been admixed with other components to form a feed gas to feed to a first reactor, a $CO/CO_2$ mole ratio between 5 and 20, whereby in said first reactor the conversion is carried out at a pressure of 5-100 bar and a temperature of 150°-400° C., preferably 200°-350° C., so as to convert the feed gas into a first intermediate containing methanol and further into a second intermediate containing dimethyl ether, after which in a second reactor at substantially the same pressure as in the first reactor and at a temperature of about 150°-600° C., preferably 300°-450° C., said second intermediate from the first reactor is converted to form hydrocarbons. According to the invention, the process is characterised by (i) forming the feed gas for the first reactor by combining ($\alpha$) a fresh synthesis gas, optionally after having subjected it wholly or partly to a wash to remove at least part of the content of $CO_2$, ($\beta$) a first recycle stream separated off from the effluent from the second reactor and containing hydrogen, carbon oxides, lower hydrocarbons and optionally inert gases, and ($\gamma$) steam in an amount such that the feed gas, when equilibrated according to the reaction (3) mentioned below, will obtain a CO/H$_2$ mole ratio of about 1, and feeding the feed gas to the first reactor, (ii) carrying out the conversion of the feed gas in said first reactor in the presence of one or more catalysts which together catalyse reactions $$CO + 2H_2 \rightleftharpoons CH_3OH, \qquad (1)$$

$$2CH_3OH \rightleftharpoons CH_3OCH_3 + H_2O, \text{ and} \qquad (2)$$

$$CO + H_2O \rightleftharpoons CO_2 + H_2, \qquad (3)$$

so as to form the abovementioned first intermediate containing methanol and then the second intermediate containing dimethyl ether, (iii) passing the entire effluent from the first reactor, combined with a second recycle stream separated off from the effluent from the second reactor and containing low-boiling constituents thereof, to the second reactor, said second reactor being an adiabatic reactor, (iv) subjecting the gases thus introduced into the second reactor to the second synthesis step in the presence of at least one catalyst which catalyses the conversion of the combined stream of effluent from the first reactor and the second recycle stream into a gas mixture containing hydrocarbons, and (v) dividing the effluent from the second reactor into several streams as follows:

(a) a stream, mainly containing water and being conducted away, (b) a purge stream containing hydrogen, carbon oxides, lower hydrocarbons and inert gases, which is conducted away, (c) the first recycle stream, having the same composition as the purge stream (b), and being recycled so as to form component ($\beta$) of the feed gas fed to the frist reactor, at least part of said first recycle stream being subjected to a wash to remove part of the content of CO$_2$ therein so as to ensure, optionally together with wash of part of the fresh synthesis gas denoted component ($\alpha$), the desired mole ratio CO/CO$_2$ of 5 to 20 in the feed gas, (d) the second recycle stream containing low-boiling components of said effluent from the second reactor, and (e) at least one stream containing the desired product of hydrocarbons.

BRIEF DESCRIPTION OF THE DRAWING

The invention will be readily understood from the accompanying drawing, which shows a flow diagram for the reactions according to the invention.

In the drawing, 5 denotes a stream of fresh synthesis gas. The synthesis gas will normally originate from a gasification of coal but may also be prepared from other raw materials. At any rate, the fresh synthesis gas contains hydrogen and carbon oxides and has a CO/H$_2$ mole ratio above 1. It may be passed in its entirety, as shown by 5$a$, into a first reactor 1, thereby by-passing a washing step 4, or part or all of it may pass the washing step 4 in which the gas is more or less freed from carbon dioxide. There are many well-known manners to carry out such CO$_2$-wash, e.g. by aid of the socalled "Selexol" process. It is also possible to use for instance amines or carbonates to achieve some removal of CO$_2$. Before being passed into first reactor 1 the fresh feed gas is admixed with a first or "outer" recycle stream 12 separated off from the effluent from the second reactor and containing hydrogen, carbon oxides, lower hydrocarbons and inert gases. A part 12$a$ or all of this first recycle stream may be subjected to CO$_2$-wash in washing step 4, and another part 12$b$ may be admixed directly with the fresh synthesis gas. The proportion of part stream 12$a$ to part stream 12$b$ is chosen such that a final feed stream 6 to the first reactor 1 has the desired mole ratio CO/CO$_2$ of 5 to 20, it being taken into account that even part of the fresh synthesis gas may be subjected to this CO$_2$-wash. The stream 6 to the first reactor 1 is also supplemented with a stream of steam 7, this to ensure that the gas stream 6 fed to reactor 1 will obtain a CO/H$_2$ mole ratio of about 1 when the feed stream has been equilibrated according to the above reaction (3).

In reactor 1, which is preferably a cooled reactor, but which may be an adiabatic reactor, the reactions are carried out as mentioned hereinabove and the entire effluent 8 from reactor 1 is passed to the second reactor 2, which is an adiabatic reactor, after having being mixed with a second or "inner" recycle stream 9 separated off from the effluent from said second reactor 2. The effluent 10 from reactor 2 is passed to a separator 3 which in known manner separates the effluent 10 into several streams as mentioned hereinabove, i.e. a side stream 11 mainly containing water and being conducted away; the abovementioned first recycle stream 12 containing hydrogen, carbon oxides, lower hydrocarbons and inert gases; a purge stream 13 having the same composition as the first recycle stream 12; second recycle stream containing low-boiling constituent of effluent 10; and at least one stream 14 of the desired hydrocarbon product.

DETAILED DESCRIPTION OF THE INVENTION

As will be understood, the invention relates to a catalytic process for preparing hydrocarbons by converting a synthesis gas containing hydrogen and carbon oxides at a mole ratio CO/H$_2$ above 1, which comprises, in combination, the steps of (i) forming a feed gas by combining ($\alpha$) a synthesis gas, optionally after having subjected it wholly or partly to a wash to remove at least some carbon dioxide therefrom, ($\beta$) a first recycle stream separated off from the effluent from a second reactor as defined below, said first recycle stream containing hydrogen, carbon oxides, lower hydrocarbons and optionally inert gases, and ($\gamma$) steam in an amount such that the feed gas, when equilibrated according to the reaction (3) defined below, will obtain a CO/H$_2$ mole ratio of about 1, the content of CO$_2$ in the fresh synthesis gas and the first recycle stream being adjusted so as to obtain a mole ratio CO/CO$_2$ of 5 to 20 in the feed gas thus formed, i.e. before the equilibration according to the reaction (3), (ii) passing the feed gas thus formed to a first reactor and converting it in said first reactor at a pressure of 5–100 bar and a temperature of 150°–400° C. in the presence of one or more catalysts which together catalyse the reactions $$CO + 2H_2 \rightleftharpoons CH_3OH, \qquad (1)$$

$$2CH_3OH \rightleftharpoons CH_3OCH_3 + H_2O, \text{ and} \qquad (2)$$

$$CO + H_2O \rightleftharpoons CO_2 + H_2 \qquad (3)$$

to form a first intermediate containing methanol and in said first reactor converting at least a substantial part of the methanol further into dimethyl ether so as to form a second intermediate containing dimethyl ether, (iii) passing the entire effluent from said first reactor to an adiabatic, second reactor after having combined said effluent with a second recycle stream separated off from the effluent from said second reactor, said second recycle stream containing low-boiling constituents, (iv) to complete in said reactor at substantially the same pressure as in the first reactor and at a temperature of about 150°–600° C. the conversion of the synthesis gas in the presence of at least one catalyst which catalyses the conversion of the gas fed to said second reactor into a gas mixture containing hydrocarbons, and (v) dividing the effluent from the second reactor into several streams as follows:

(a) a stream, mainly containing water and being conducted away, (b) a purge stream containing hydrogen, carbon oxides, lower hydrocarbons and inert gases and being conducted away, (c) the first recycle stream, having the same composition as the purge stream (b), and being recycled so as to form component ($\beta$) of the feed gas for the first reactor, at least part of said first recycle stream being subjected to a wash to remove part of the content of $CO_2$ therein so as to ensure, optionally together with wash of part of the fresh synthesis gas denoted component ($\alpha$), the desired mole ratio $CO/CO_2$ of 5 to 20 in the feed gas, (d) the second recycle stream containing low-boiling components of said effluent from the second reactor, and (e) at least one stream containing the desired product of hydrocarbons.

The $CO_2$-wash as mentioned has for its purpose to permit the adjustment of a $CO/CO_2$ mole ratio between 5 and 20 in the feed stream to the first reactor. This adjustment according to the invention may take place by fully or partly washing firstly the fresh synthesis gas and secondly the first, outer recycle stream. In practice the removal of $CO_2$ takes place to the desired degree by varying the efficiency of the $CO_2$-wash, and/or by subdividing the fresh synthesis gas stream into a part stream (5b) passing the $CO_2$-wash and another part stream (5a) by-passing the $CO_2$-wash, and/or by subdividing the first recycle stream (12) into a part stream (12a) passing the $CO_2$-wash and a part stream (12b) by-passing the $CO_2$-wash. If the fresh synthesis gas contains sulfur, e.g. a coal gasification gas, it can conveniently be removed by subjecting the entire stream of fresh synthesis gas to a washing operation.

By using in the first reactor one or more catalysts having activity for the reactions (1) and (2) as well as the reaction (3), as stated hereinabove, combined with the use of a synthesis gas having a mole ratio $CO/H_2$ above 1 as stated, it is obtained that the first step conversion in the process according to the invention proceeds without the formation of excess of water, substantially according to the overall reaction:

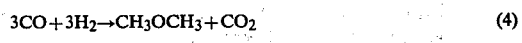

$$3CO + 3H_2 \rightarrow CH_3OCH_3 + CO_2 \qquad (4)$$

It is a considerable advantage that the formation of water in excess is hereby avoided since the formation of water firstly entails an energy loss for condensation and secondly in certain cases may necessitate the removal of water between the first and the second process step because certain of the catalysts usable in the second step to a certain degree may be deactivated by steam.

If instead one employs the conventional technique and conducts the reaction (3) in a separate reactor and the reactions (1) and (2) in a subsequent reactor, the water formed in reaction (2) could not be employed for carrying out reaction (3). Consequently there must be supplied a larger amount of water from the outside to accomplish (3) to obtain a $CO/H_2$ mole ratio of 0.5, which is necessary to accomplish reactions (1) and (2). The outlet stream from the first step accordingly will contain the water formed in reaction (2).

On the other hand the accomplishment of the conversion in the first step according to equation (4) requires the use of a suitable synthesis gas, i.e. a synthesis gas having a $CO/H_2$ mole ratio above 1 as stated hereinbefore. The invention therefore is directly usable and particularly advantageous for the conversion of synthesis gases obtained by the gasification of coal because such gases have the desired composition. However, the invention may find use in the conversion of any synthesis gas adjusted to the stated $CO/H_2$ mole ratio.

A further advantage in conducting the conversion in the first step of the process according to the invention according to reaction (4) is the high $CO_2$-content obtained in the product gas from this step. The high content of $CO_2$ acts as a dilution of the gas and moreover gives it a higher specific heat whereby it is possible to reduce the amount of the inner recycle stream of product gas around the second step of the process where the highly exothermal conversion on DME into gasoline takes place.

Beyond the advantages which as mentioned are obtained by carrying out the conversion in the first step according to equation (4), i.e. with equimolar amounts of carbon monoxide and hydrogen, it should be emphasized that it is easy to accomplish the adjustment of the composition of the synthesis gas which is the prerequisite therefore, since it merely requires an adjustment of the amount of steam conducted to the first step.

The amount of steam which it is necessary to add to adjust a given synthesis gas at a $CO/H_2$ ratio of 1 can be calculated from the abovementioned reaction (3).

If, for instance, there is used an anhydrous synthesis gas having a $CO/H_2$ ratio of 2, it thus can be calculated that 0.5 mole of steam must be added per mole of CO. If the synthesis gas has a $CO/H_2$ ratio of 4, there must be added 1.5 mole of $H_2O$ per mole of CO.

Although synthesis gases having a high $CO/H_2$ mole ratio may be used in principle in the process according to the invention, in practice one will prefer $CO/H_2$ mole ratios between 1 and 4.

The first step in the process according to the invention may be carried out at a pressure of 5–100 bar, preferably 20–60 bar, and a temperature of 150°–400° C., preferably 200°–350° C. The pressure to employ in any given case will depend on several factors. Generally it is preferable to carry out the conversion at the pressure at which the synthesis gas is available. If, for instance, the synthesis gas has been obtained by gasification of coal, the pressure at present day's technique will be of the order of magnitude 30 bar. It can be expected, however, that future technique will render higher pressures possible, e.g. 70 bar or more. Even if increased pressure involves some increase of the degree of conversion, it will generally be preferable to operate at the gasification pressure because compression work is thereby saved. It is the comparatively low pressure dependency of the DME synthesis that renders this possible.

Even the temperature to choose will depend upon the practical embodiment, in the first place whether the conversion is operated in an adiabatic or in a cooled reactor. When using an adiabatic reactor one must accept a higher outlet temperature and hence a lower degree of conversion since the lower limit of the inlet temperature is determined by the activity of the catalyst employed. When using a cooled reactor it is on the other hand possible to maintain the temperature in the entire reactor within a narrow temperature range and accordingly it is possible to optimize the temperature with regard to the other process parameters. Accordingly it is preferred to carry out the first step of the instant process in a cooled reactor. Any form of cooled reactor may be employed. A particularly preferred reactor, however, is a reactor containing catalyst filled tubes surrounded by boiling water as coolant. By using such a reactor there will be a possibility of utilizing the heat liberated in the first step to generate steam.

The catalyst or catalysts used in the first step as mentioned must have activity for reactions (1), (2) and (3) at the temperature employed according to the invention. For instance there may be used a single composite catalyst having activity for all of the reactions, or two catalysts one of which is a catalyst having activity for reactions (1) and (3) and the other a catalyst having activity for reaction (2). As examples of usable catalysts may be mentioned the socalled methanol catalysts, of which several have catalytic activity for reaction (1) as well as reaction (3); and the socalled acidic dehydration catalysts which catalyze reaction (2).

By laboratory experiments it has been found that for reactions (1) and (3) one can advantageously use oxides of zinc and chromium, oxides of zinc and aluminum, oxides of copper, chromium and zinc, or oxides of copper and zinc and aluminum. Such catalysts are known. The metal oxides mentioned may be composite or complex oxides where the two or three metals are chemically and/or physically combined in one oxidic structure.

For reaction (2) it has been found by laboratory experiments that alumina ($Al_2O_3$) or alumina-containing catalysts are suitable. One possible such catalyst is a combination of alumina, such as $\gamma$-alumina, with silica ($SiO_2$), and also certain zeolites are useful for this reaction.

The catalysts may be used in the form of a mixture of particles containing a catalyst with activity for the reactions (1) and (3) and particles containing a catalyst with activity for the reaction (2) or they may be used in the form of particles each of which are containing both types of catalysts.

The second step in the process according to the invention is preferably carried out at substantially the same pressure as that used in the first step, and at a temperature from about 150° C. to about 600° C., preferably 300°–450° C. Some pressure drop is inevitable, and it is unnecessary and uneconomic to raise it; therefore, in practice the pressure will be about 2 bar lower in the second than in the first reactor. The conversion is carried out in an adiabatic reactor whereby recycling a part of the product gas, the socalled inner recycle stream, back to the inlet of the reactor is employed in order to limit the temperature increase since this reaction is strongly exothermal.

The conversion is carried out in the presence of a catalyst having selectivity for the hydrocarbon fraction desired as the product. As catalyst one can, e.g., use catalysts of the kind where the selectivity of the catalyst is connected with its chemical composition and physical structure, especially pore structure. As examples of catalysts of this kind may for instance be mentioned synthetic zeolites, a large number of forms thereof being known and some of them described, i.a., in the above-mentioned U.S. Pat. Nos. 3,702,886, 3,709,979 and 3,832,449.

The size of the recycle streams may vary inside wide limits depending on various process parameters. Thus the size of the outer recycle stream is chosen so as to obtain the desired total conversion and the size of the inner recycle stream will be chosen so as to limit the temperature increase in the second reactor. Typical ratios between the outer recycle stream and the fresh synthesis gas will be from 1 to 10, and between the inner recycle stream and the effluent from the first reactor will be from 1 to 8.

In the following the process according to the invention will be illustrated more detailedly by a calculated Example.

EXAMPLE

The process described above is carried out using a synthesis gas obtained by gasification of coal by known technique. The present calculation is based on a gas composition corresponding to that of a gas obtained by coal gasification using a Texaco gasifier.

The crude synthesis gas is freed from sulfur and possible other impurities whereby there is obtained a synthesis gas having the composition 5 (see the Table below).

This composition as well as the following compositions are numbered as the gas streams in the drawing.

A stream of this synthesis gas of 156,880 $Nm^3/h$ and an outer recycle stream of synthesis gas of 210,740 $Nm^3/h$ are passed through a $CO_2$-wash to partly remove $CO_2$. The feed stream of synthesis gas obtained after the $CO_2$-wash, amounting to 330,600 $Nm^3/h$ and having the composition 6 (cf. the Table) is passed together with 10,525 kg/h of steam to a first, cooled, reactor in which the conversion onto MeOH/DME is carried out at a pressure of 32 bar and a temperature of 280° C.

There is obtained an outlet stream of 243,110 $Nm^3/h$ having the composition 8 (cf. the Table) and this is passed together with an inner recycle stream of 385,580 $Nm^3/h$ to a second, adiabatic, reactor in which the conversion into hydrocarbons is carried out at an inlet temperature of 340° C. and an outlet temperature of 420° C.

There is obtained an outlet stream of 637,440 $Nm^3/h$ and having the composition 10 (cf. the Table).

The outlet stream from the second reactor in known manner is subdivided into the following streams:
a side stream of water of 18,917 kg/h;
an inner recycle stream of 385,580 $Nm^3/h$ and having the composition 9 (cf. the Table);
a stream having the composition 12/13 (cf. the Table), which is subdivided into an outer recycle stream of 210,740 $Nm^3/h$ and a side stream (purge) of 9644 $Nm^3/h$;
a first product stream of 3645 $Nm^3/$having the composition 14a (cf. the Table);
a second product stream of 2114 $Nm^3/h$ and having the composition 14b (cf. the Table); and a third product stream of 2187 Nm³/h and having the composition 14c (cf. the Table).

TABLE

| Composition No. | Compositions of gas streams, mole % | | | | | | | | |
|---|---|---|---|---|---|---|---|---|---|
| | 5 | 6 | 8 | 10 | 9 | 12/13 | 14a | 14b | 14c |
| H₂ | 35.8 | 31.9 | 21.1 | 21.9 | 22.8 | 23.0 | | | |
| H₂O | 0 | 4.0 | 0.4 | 3.7 | 0 | 0 | | | |
| CO | 50.6 | 39.8 | 22.5 | 23.2 | 24.3 | 24.1 | | | |
| CO₂ | 12.3 | 5.7 | 21.4 | 22.1 | 23.1 | 25.3 | | | |
| CH₄ | 0.3 | 7.7 | 10.5 | 11.1 | 11.6 | 11.7 | | | |
| MeOH | | | 0.5 | | | | | | |
| DME | | | 8.8 | | | | | | |
| nC₂-C₄ | | | | 1.5 | 1.5 | | 100 | | |
| nC₅ + iC₄-C₆ | | | | 0.7 | 0.6 | | | 100 | |
| C₇-C₈ aromatics | | | | 0.4 | 0.1 | | | | 100 |
| Ar + N₂ | 1.0 | 10.9 | 14.9 | 15.4 | 16.1 | 16.0 | | | |

We claim:

1. A catalytic process for preparing hydrocarbons that by converting a synthesis gas containing hydrogen and carbon oxides at a mole ratio CO/H₂ above 1, which comprises, in combination, the steps of
   (i) forming a feed gas by combining
   (α) a synthesis gas, optionally after having subjected it wholly or partly to a wash to remove at least some carbon dioxide therefrom,
   (β) a first recycle stream separated off from the effluent from a second reactor as defined below, said first recycle stream containing hydrogen, carbon oxides, lower hydrocarbons and optionally inert gases, and
   (γ) steam in an amount such that the feed gas, when equilibrated according to the reaction (3) defined below will obtain a CO/H₂ mole ratio of about 1, the content of CO₂ in the fresh synthesis gas and the first recycle stream being adjusted so as to obtain a mole ratio CO/CO₂ of 5 to 20 in the feed gas thus formed,
   (ii) passing the feed gas thus formed to a first reactor and converting it in said first reactor at a pressure of 5–100 bar and a temperature of 150°–400° C. in the presence of one or more catalysts which together catalyse the reactions $$CO + 2H_2 \rightleftharpoons CH_3OH, \quad (1)$$

$$2CH_3OH \rightleftharpoons CH_3OCH_3 + H_2O, \text{ and} \quad (2)$$

$$CO + H_2O \rightleftharpoons CO_2 + H_2 \quad (3)$$

to form a first intermediate containing methanol and in said first reactor converting at least a substantial part of the methanol further into dimethyl ether so as to form a second intermediate containing dimethyl ether,
   (iii) passing the entire effluent from said first reactor to an adiabatic, second reactor after having combined said effluent with a second recycle stream separated off from the effluent from said second reactor, said second recycle stream containing low-boiling constituents,
   (iv) to complete in said reactor at substantially the same pressure as in the first reactor and at a temperature of about 150°–600° C. the conversion of the synthesis gas in the presence of at least one catalyst which catalyses the conversion of the gas fed to said second reactor into a gas mixture containing hydrocarbons, and
   (v) dividing the effluent from the second reactor into several streams as follows:
   (a) a stream, mainly containing water and being conducted away,
   (b) a purge stream containing hydrogen, carbon oxides, lower hydrocarbons and inert gases and being conducted away,
   (c) the first recycle stream, having the same composition as the purge stream (b), and being recycled so as to form component (β) of the feed gas for the first reactor, at least part of said first recycle stream being subjected to a wash to remove part of the content of CO₂ therein so as to ensure, optionally together with wash of part of the fresh synthesis gas denoted component (α), the desired mole ratio CO/CO₂ of 5 to 20 in the feed gas,
   (d) the second recycle stream containing low-boiling components of said effluent from the second reactor and
   (e) at least one stream containing the desired product of hydrocarbons.

2. A process as claimed in claim 1, wherein the entire amount of fresh synthesis gas and a part of the first recycle stream are subjected to a washing process to remove CO₂, the amount of the part of said first recycle stream to be washed being chosen so as to ensure the desired mole ratio of 5 to 20 in the feed stream to the first reactor.

3. A process as claimed in claim 2, wherein CO₂ is removed from fresh synthesis gas containing CO₂ and the part of the first recycle stream from which to remove the CO₂ are combined before the washing so as to carry out the CO₂-wash in one operation.

4. A process as claimed in claim 1, in which the first reactor is a cooled reactor.

5. A process as claimed in claim 4, in which the cooled reactor contains catalyst-filled tubes surrounded by boiling water as coolant.

6. A catalytic process for preparing hydrocarbons that are liquid at normal temperature and pressure by converting a synthesis gas containing hydrogen and carbon oxides at a mole ratio CO/H₂ above 1, and a mole ratio CO/CO₂ of 5 to 20, which comprises, in combination, the steps of
   (i) forming a feed gas by combining
   (α) a synthesis gas, optionally after having subjected it wholly or partly to a wash to remove at least some carbon dioxide therefrom,
   (β) a first recycle stream separated off from the effluent from a second reactor as defined below, said first recycle stream containing hydrogen, carbon oxides, lower hydrocarbons and optionally inert gases, and
   (γ) steam in an mount such that the feed gas, when equilibrated according to reaction (3) defined below, will obtain a CO/H₂ mole ratio of about 1, the content of CO₂ in the fresh synthesis gas and the first recycle stream being adjusted so as to obtain a mole ratio CO/CO₂ of 5 to 20 in the feed gas thus formed,
   (ii) passing the feed gas thus formed to a first reactor and converting it in said first reactor at a pressure of 5–100 bar and a temperature of 150°–400° C. in the presence of one or more catalysts which together catalyse the reactions $$CO + 2H_2 \rightleftharpoons CH_3OH, \quad (1)$$

$$2CH_2OH \rightleftharpoons CH_3OCH_3 + H_2O, \text{ and} \quad (2)$$

$$CO + H_2O \rightleftharpoons CO_2 + H_2 \quad (3)$$

to form a first intermediate containing methanol and in said first reactor converting at least a substantial part of the methanol further into dimethyl ether so as to form a second intermediate containing dimethyl ether,
(iii) passing the entire effluent from said first reactor to an adiabatic, second reactor after having combined said effluent with a second recycle stream separated off from the effluent from said second reactor, said second recycle stream containing low-boiling constituents,
(iv) to complete in said reactor at substantially the same pressure as in the first reactor and at a temperature of about 150°–600° C. the conversion of the synthesis gas in the presence of at least one catalyst which catalyses the conversion of the gas fed to said second reactor into a gas mixture containing hydrocarbons that are liquid at normal temperature and pressure,
(v) dividing the effluent from the second reactor into several streams as follows:
(a) a stream, mainly containing water and being conducted away,
(b) a purge stream containing hydrogen, carbon oxides, lower hydrocarbons and inert gases and being conducted away,
(c) the first recycle stream, having the same composition as the purge stream (b), and being recycled so as to form component ($\beta$) of the feed gas for the first reactor, at least part of said first recycle stream being subjected to a wash to remove part of the content of $CO_2$ therein so as to ensure, optionally together with wash of part of the fresh synthesis gas denoted component ($\alpha$), the desired mole ratio $CO/CO_2$ of 5 to 20 in the feed gas,
(d) the second recycle stream containing low-boiling components of said effluent from the second reactor, and
(e) at least one stream containing the desired product of hydrocarbons being liquid at normal temperature and pressure.

7. A process as claimed in claim 6, wherein the entire amount of fresh synthesis gas and a part of the first recycle stream are subjected to a washing process to remove $CO_2$, the amount of the part of said first recycle stream to be washed being chosen so as to ensure the desired mole ratio of 5 to 20 in the feed stream to the first reactor.

8. A process as claimed in claim 7, wherein $CO_2$ is removed from fresh synthesis gas containing $CO_2$ and the part of the first recycle stream from which to remove the $CO_2$ are combined before the washing so as to carry out the $CO_2$-wash in one operation.

9. A process as claimed in claim 6, in which the first reactor is a cooled reactor.

10. A process as claimed in claim 9, in which the cooled reactor contains catalyst-filled tubes surrounded by boiling water as coolant.

* * * * *